United States Patent [19]
Peik et al.

[11] Patent Number: 5,175,278
[45] Date of Patent: Dec. 29, 1992

[54] HETEROPOLYSACCHARIDE S-657

[75] Inventors: Jerry A. Peik, San Diego; Suzanna M. Steenbergen, Alpine; George T. Veeder, San Diego, all of Calif.

[73] Assignee: Merck & Co., Inc., Rahway, N.J.

[21] Appl. No.: 577,824

[22] Filed: Sep. 4, 1990

Related U.S. Application Data

[63] Continuation of Ser. No. 215,000, Jul. 5, 1988, abandoned, which is a continuation of Ser. No. 750,704, Jun. 28, 1985, abandoned.

[51] Int. Cl.$^5$ .................... C07G 17/00; C12P 19/04; C12N 1/20
[52] U.S. Cl. .................... 536/123; 536/55.1; 435/101; 435/252.1; 435/910; 252/8.551
[58] Field of Search .................... 536/55.1, 114, 119, 536/123; 252/8.551; 435/101, 252.1, 910

[56] References Cited

U.S. PATENT DOCUMENTS

| | | | |
|---|---|---|---|
| 3,485,719 | 12/1969 | Rogovin | 435/910 |
| 4,326,053 | 4/1982 | Kang | 536/1 |
| 4,352,741 | 10/1982 | Wernau | 435/101 |
| 4,401,760 | 8/1983 | Peik et al. | 435/101 |

FOREIGN PATENT DOCUMENTS 0130647 1/1985 European Pat. Off. .

OTHER PUBLICATIONS

Yakovlev, A. I. et al., CA 98: 104345 (1983) Kaplan, N. et al., *Appln. Environ. Microbiol.* 44(6), pp. 1335–1341 (1982).
Kang, K. et al., *Appln. Environ. Microbiol.* 43(6), pp. 1335–1341 (1982).
Josaleau, J. P. et al., *Carbohydr. Res.* 101(2), pp. 175–181 (1982).
Prakobphol, A. et al., *Infect. Immu.* 27(1), pp. 150–157 (1980).
Pazur, J. H. et al., *Carbohydr. Res.* 66, pp. 155–166 (1978).
Dutton, G. S. et al., *Carbohydr. Res.* 65, pp. 251–263 (1978).
Roy, N., *Carbohydr. Res.* 63, pp. 333–336 (1978).
Mamatov, G. Z. et al., CA 85: 90165q (1975).
Lindberg, G., *Carbohydr. Res.* 48, pp. 81–84 (1976).
Wetherell, J. R. et al., CA 84:87821Z (1975).
Choy, Y. M. et al., *Can. J. Chem.* 52 (4), pp. 684–687 (1974).
M. O'Neill et al., Carbohydrate Research, vol. 124 No. 1, 123–133 (1983).
Jansson et al., Carbo. Res., 45, 275–282 (1975).
Chowdhury et al., Carbo. Res., 164 117–122 (1987).

*Primary Examiner*—Irene Marx
*Attorney, Agent, or Firm*—Charles M. Caruso; Gabriel Lopez; Richard S. Parr

[57] ABSTRACT

The new heteropolysaccharide S-657, prepared by fermentation of a new strain of *Xanthomonas campestris*, ATCC 53159, has valuable properties as a thickening, suspending and stabilizing agent in aqueous solutions and is especially valuable for use in well treating fluids.

Heteropolysaccharide S-657 is composed principally of carbohydrate, about 12% protein and about 7% (calculated as O-acetyl) acyl groups, the carbohydrate portion containing about 19% glucuronic acid, and the neutral sugars rhamnose and glucose in the approximate molar ratio of 2:1.

2 Claims, No Drawings

HETEROPOLYSACCHARIDE S-657

This is a continuation of application Ser. No. 07/215,000 filed Jul. 5, 1988, now abandoned, which is a continuation of application Ser. No. 06/750,704 filed Jun 28, 1985, now abandoned.

BACKGROUND OF THE INVENTION

This invention pertains to the field of microbial polysaccharides In this field, it is known that a common feature of certain microorganisms is the production of exocellular heteropolysaccharides. Heteropolysaccharides are high molecular weight generally linear carbohydrate polymers containing two or more kinds of monosaccharides that form a repeating unit that is polymerized.

The usefulness of most heteropolysaccharides is based on their ability to alter the viscosity and rheology of aqueous solutions. In addition, heteropolysaccharides have related secondary functions, such as emulsification, suspension, stabilization, flocculation, etc. See for example, U.S. Pat. Nos. 4,326,052 and 4,401,760.

Heteropolysaccharides are widely used in food, well drilling, agricultural and a wide variety of other industrial applications. Commercial demand for these water soluble gums has greatly increased over the last few decades. Furthermore, new industrial techniques create a need for heteropolysaccharides with new physical properties. Consequently, the need for heteropolysaccharides with different functionality ranges, coupled with commercial demand, has clearly indicated the necessity for the development of new heteropolysaccharides with new and different physical properties.

It is, therefore, an object of the present invention to provide a new heteropolysaccharide, which is produced by a new strain of the microorganism *Xanthomonas campestris*. It is an additional object of the present invention to provide a method for making this new heteropolysaccharide. It is another object to provide microorganisms for making the new compound. A still further object is the provision of formulations containing the new heteropolysaccharide. These and other objects of the invention will be apparent from the ensuing description.

SUMMARY OF THE INVENTION

It has now been found that a novel heteropolysaccharide, composed principally of carbohydrate, about 12% protein and about 7% (calculated as O-acetyl) acyl groups, the carbohydrate portion containing about 19% by weight glucuronic acid and the neutral sugars rhamnose and glucose in the approximate molar ratio of 2:1, is produced by the action of a new strain of *Xanthomonas campestris* on a selected carbon source. This novel compound is prepared by aerobic fermentation of a suitable aqueous nutrient medium with the new strain of *Xanthomonas campestris*. A deposit under the Budapest Treaty of a biologically pure culture of this organism was made with the American Type Culture Collection, Rockville, Maryland, on June 19, 1985 under Accession No. ATCC 53159. This heteropolysaccharide, referred to herein as heteropolysaccharide S-657, has desirable properties in aqueous systems and is especially useful in formulating oil well treating fluids.

DETAILED DESCRIPTION OF THE INVENTION

The novel organism of the present invention was isolated from an algal sample taken from a marsh near Eureka, California. The organism was picked as a gummy colony from a YM agar plate after 4 days of incubation at 30° C. The isolate was then pure cultured on nutrient agar.

A flask seed was started from a nutrient agar culture of the isolate. This seed was then used to inoculate another flask containing a nutrient medium having hydrolyzed starch as the carbon source. After incubation, this flask was noted to contain a viscous beer and upon addition of isopropyl alcohol a fibrous material was precipitated. Another flask seed was started and used to determine the effect of various nutrient media on gum production and to determine the best growth media and fermentation conditions for this microorganism.

Fermentation Conditions

Heteropolysaccharide S-657 is produced during the aerobic fermentation of suitable aqueous nutrient media under controlled conditions via inoculation with a culture of the organism ATCC 53159. The media contain sources of assimilable carbon, nitrogen, and inorganic salts.

In general, carbohydrates (for example, glucose, fructose, maltose, sucrose, xylose, lactose and the like) can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 2% and 5% by weight of the medium. These carbon sources may be used individually or combined in the medium.

Generally, many proteinaceous materials may be used as nitrogen sources for the fermentation process. Suitable nitrogen sources include, for example, yeast hydrolysates, primary yeast, soybean meal, cottonseed flour, hydrolysates of casein, cornsteep liquor, distiller's solubles or tomato paste and the like. The sources of nitrogen, either alone or in combination, are used in amounts preferably ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the nutrient media described herein are merely illustrative of the wide variety of media which may be employed, and are not intended to be limiting.

As an alternate medium, S-657 may be grown under low calcium ion conditions, i.e., in deionized water or some other aqueous system substantially free of calcium ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the ATCC 53159 culture and producing the heteropolysaccharide S-657 can vary from about 6 to 8.

Although S-657 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing S-657 is particularly suited for the preparation of large quantities.

Heteropolysaccharide S-657

The heteropolysaccharide produced by ATCC 53159 is composed principally of carbohydrate, about 12% protein and about 7% by weight (calculated as O-acetyl) acyl groups, and substantially no pyruvate. The carbohydrate portion of S-657 contains about 19% glucuronic acid (based on weight of gum) and the neutral sugars rhamnose and glucose in the approximate molar ratio of 2:1.

The acetyl content of about 7% was determined by two separate techniques. A 0.2% aqueous solution of S-657 gum was treated with an alkaline, hydroxylamine reagent followed by treatment with an acidic ferric chloride reagent and colorimetric analysis [See S. Hestrin (1949) *J. Biol. Chem.* 180, 249-261]. The O-acyl group was identified as O-acetyl and determined by liquid chromatography.

The neutral sugars of S-657 were also determined by various techniques. One method involves hydrolyzing 50 mg of S-657 in 1 ml of 1M $H_2SO_4$ at 100° C. for 4 hours. After cooling, 0.5 ml of 3 mg/ml xylose was added as an internal standard. Samples were neutralized by adding 3 ml of saturated $Ba(OH)_2$, then two drops of Congo Red and $Ba(OH)_2$ until the color changed to red. After centrifuging (20 minutes at 3000 RPM) the supernatants of all samples were evaporated. Dry samples were dissolved in 0.1 ml of hydroxylamine hydrochloride (40 mg/ml in dry pyridine) and heated at 90° C. for 45 minutes. After cooling 0.1 ml acetic anhydride is added and the samples again heated at 90° C. for 45 minutes. The sugars were separated by gas-liquid chromatography of their aldononitrile acetate derivatives and were identified and quantified by comparison with authentic standards [J. K. Baird, M. J. Holroyde, and D. C. Ellwood (1973) *Carbohydr. Res.* 27, 464–467].

The various neutral sugars of this polysaccharide were also characterized by a second method which involves dissolving approximately 2 mg of S-657 in 0.5M trifluoroacetic acid (2 ml). The sample was kept at 100° C. overnight, concentrated to dryness and dissolve in water (2 ml). Sodium borohydride (25 mg) was added and after 2 hours the solution was treated with Dowex 50 ($H^+$) after which the pH dropped to 3.5. After filtration, the solution was concentrated and codistilled with methanol (3×5 ml). The residue was dissolved in a mixture of acetic anhydride (1 ml) and pyridine (1 ml), kept at 100° C. for 1 hour and concentrated. After codistillation with toluene (3×5 ml), the residue was dissolved in methylene chloride and analyzed by gas-liquid chromatography.

TABLE 1

| Total Neutral Sugars in S-657 | | |
|---|---|---|
| | Mole Percent Rhamnose | Mole Percent Glucose |
| Method 1 (3 samples) | 57 | 43 |
| Method 2 (9 samples) | 64 | 36 |

The glycuronic acid content of the polysaccharide was determined by decarboxylation with 17% hydrochloric acid, followed by trapping the liberated carbon dioxide in standard sodium hydroxide and back titration [B. L. Browning (1967) *Methods of Wood Chemistry* 2, 632–633]. The decarboxylation method gave values between 17.6% and 19.6% for three different samples of S-657.

Paper electrophoresis was used for the separation and identification of the uronic acids present in the neutralized acid hydrolysate described above. Aliquots of this and known uronic acid standards were applied to electrophoresis paper and electrophoresis was carried out for 2 hours in a pH 2.7 buffer. Chromatograms were air dried and stained with silver nitrate to locate the uronic acids being separated. The only confirmed uronic acid spot was found to be glucuronic acid.

The absence of pyruvate was determined by adding 1 ml of a 2 mg/ml solution of S-657 to a culture tube, and adding 1 ml of 0.2N HCl, and heating at 100° C. for 4 hours. A 0.5 ml sample of hydrolysate was added to 0.1 ml of reduced diphosphopyridine nucleotide (NADH) and 2.4 ml of triethanolamine solution. The absorbance was detected on a spectrophotometer and pyruvate measured. [Duckworth and Yaphe *Chem. & Ind.* (1970) p. 747.] No significant pyruvate was detected.

Nitrogen analysis was performed by Kjeldahl digestion and was determined as about 1.5% by weight nitrogen (between about 1.3% and 1.9% for 3 samples). Solids and ash analysis showed S-657 contained about 94% by weight solids (91.8%-95.8%) and 9% (7.8-10.3%) by weight ash. The protein content was determined to be about 12% (7.5%-14.5%) by the method of Lowry et al., [*J. Biol. Chem.*, (1951), 193, p. 256], using bovine serum albumin as standard.

Methylation analysis was performed on partially purified samples of S-657 after dialysis and freeze drying. The samples were methylated according to the procedures outlined in Sandford & Conrad, (1966) *Biochem.* 5

1508-1507. The O-methyl ether derivatives of the sugars as their aditol acetates were separated by gas chromatography and identified by computer matching with authentic standards. The major methylated sugars identified are shown in Table 2, below.

TABLE 2

O-Methyl Sugars in Hydrolysate of Methylated S-657

| Methylated Sugar | Linkage |
|---|---|
| 2,3,4 Me$_3$ Rhamnose | 1 |
| 2,3 Me$_2$ Rhamnose | 1,4 |
| 2,4 Me$_2$ Glucose | 1,3,6 |
| 2,6 Me$_2$ Glucose | 1,3,4 |

It is to be understood that, although the methods of analysis of the heteropolysaccharide described herein were the actual methods used in arriving at the composition described above, other methods of analysis are available to one skilled in the art. Utilization of other methods of analysis should result in the same characterization of the heteropolysaccharide, however, slightly different quantitative results may be reported.

Heteropolysaccharide S-657 has been found to have outstanding properties in aqueous solution, especially in having very high viscosity at very low concentrations, good temperature stability and good foam stability. Because of this, it is useful as a thickening, suspending, emulsifying, stabilizing, lubricating, film-forming, or binding agent. S-657 has utility in various industrial, petroleum and food applications where high viscosity and excellent thermal and foam stability are desirable. In particular it has uses in the following applications or products: adhesives, wall joint cements, water-retentive grouts and mortars, spackling compounds, can sealants, boiler compounds, latex creaming, welding-rod fluxes, braising pastes, ceramic glazes and extrusions, cleaners and polishers, toys, emulsions (latex, asphalt, silicone), silver recovery, seed coatings, spray control for pesticides or herbicides, emulsifiable concentrates and flowable pesticides and herbicides, tobacco binders, water based inks, lithographic fountain solutions, leather finishes, hydromulching and hydro-seeding, textile printing and finishing, wet-end paper additives, wet-end paper retention and formation aids, anti-slick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

This gum also has utility in food systems such as jellies and other high sugar systems, beverages including citric acid based drinks, dairy products including ice cream and yogurt, salad dressings, dry mixes, icings, and glazes, syrups, puddings, farinaceous foods, canned and retorted foods and bakery fillings.

A particularly valuable utility is in the field of petroleum and water well treating fluids and muds. Heteropolysaccharide S-657 has been found to be particularly useful in aqueous media especially formulated for use as a well treating fluid.

Well treating fluids refers to a broad spectrum of media that are used to facilitate operations during the various stages of drilling and using a well, such as a gas or oil well. The term "well treating fluids" comprises, for example, circulating drilling fluids, workover and completion fluids, coring fluids, and stimulation fluids (hydraulic fracturing and acidizing) and enhanced oil recovery fluids. Materials which may be present in such fluids include sodium chloride, potassium chloride, barium sulfate, amorphous silica, calcium carbonate, bentonite, attapulgite, sodium metasulfate, quebracho, calcium lignosulfonate, lime, calcium sulfate, calcium chloride, petroleum sulfonate, tall oil soap, crude and diesel oils, starches, biocides, and polymers such as CMC, polyacrylamides, and polyacrylates. It will be appreciated that not all of these compounds will be present in any particular fluid but, rather, that compounds will be selected by the well operator in the amount necessary for the particular task to be performed. Because of the differing underground conditions experienced during and after a well is drilled, adjustments to the well treating fluid and replacement of one fluid with another are to be expected.

S-657 has been found to exhibit properties such as high viscosity for improved suspension, heat and salt stability, shear stability, and good viscosity recovery after heating and cool-down which make it desirable as a rheology modifier in well-treating fluids.

Representative well treating fluid formulations are provided in Examples 4 and 5. These formulations are not intended to be limiting but are suggestive of a range of possible well treating fluid formulations that can be prepared with S-657. Heteropolysaccharide S-657 is usable in such formulations in the range of 0.01% to 1.0% by weight.

The high viscosity of S-657 at low concentrations makes the heteropolysaccharide particularly useful as a viscosifier for enhanced oil recovery. S-657 is usable in such operations at concentrations ranging from 0.01% to 0.2% by weight, preferably in the range of 0.02% to 0.1%.

Heteropolysaccharide S-657 has a particular profile of solution properties that is a distinctive characteristic of this polysaccharide and which enables it to be distinguished over other heteropolysaccharides. S-657 has the following profile of properties:

| I. RHEOLOGICAL DATA | | |
|---|---|---|
| 1% STW[1] Viscosity | 6 RPM, | 19500 cP |
| (Brookfield, LVF) | 60 RPM, | 2200 cP |
| | 6/60 Ratio | 8.9 |
| 0.1% STW Viscosity | 6 RPM | 95 cP |
| Brookfield LVF with | | |
| (UL adapter) | | |
| II. COMPATIBILITY DATA | | |
| [Compat. = Y, Non-Compat. = N] | | |
| Milling Green (anionic) Compat., 1% Gum Conc., Visual | | Y |
| Methylene Blue (cationic) Compat., 1% Gum Conc., Visual | | N |
| CTAB (cationic) Compat., 0.5% Gum Conc., Visual | | N |
| Cationic Latex Compat., 0.5% Gum Conc., Visual | | N |
| Cationic Surfactant Compat., 0.4% Gum Conc., Visual | | N |
| III. FUNCTIONALITY DATA | | |
| Seawater Viscosity [1 PPB (0.28% Gum Conc.), 3 RPM, Fann 35,] | | 850 cP |
| Temperature Response Test[2] [Fann 50° C. Viscometer at 100 sec$^{-1}$] | | |
| Initial viscosity at 80° F. | | 86 cP |
| Viscosity upon reaching 300° F. | | 78 cP (91%) |
| Viscosity after 1 hour at 300° F. | | 63 cP (73%) |
| Viscosity upon cooldown to 80° F. | | 73 cP (85%) |
| Saturated NaCl Viscosity [1 PPB (0.28% Gum Conc.), 3 RPM, Fann 35.] | | 20 cP |
| Saturated CaCl$_2$ Viscosity [1 PPB | | 10 cP |

-continued

| | |
|---|---|
| (0.28% Gum Conc.). 3 RPM. Fann 35] | |
| Shear Stability (1% Gum Conc.), 15 min. Blender, Init. Vis., (60 RPM)/% change | 2200 cP/+16 |
| Acrylic Latex Thickening [Latex Paint, Adhesives (PSA)] 0.5% Gum Conc. Brookfield Viscosity, 600 RPM, cP | 2250 cP |
| 6 RPM/60 RPM | 6.9 |
| Acetic acid + Heat (80° C., 2 hrs.) 0.5% Gum Conc. Init. vis. at 9.6 sec.$^{-1}$/% change 2 hr. RT/% change 2 hr. 80° C. | 1000 cP/+2/+6 |
| Heat only (80° C., 2 hrs.) 0.5% Gum. Conc. Init. vis. at 9.6 sec.$^{-1}$/% change | 1000 cP/+4 |

IV. COMMENTS AND OBSERVATIONS:

$^1$Synthetic Tap Water: Deionized water containing 1000 ppm NaCl and 147 ppm CaCl$_2$ 2H$_2$O.
$^2$0.4% Polymer in seawater containing 500 ppm Na$_2$SO$_3$.

DESCRIPTION OF THE STRAIN

Heteropolysaccharide S-657 may be prepared by fermentation of a suitable nutrient medium with a novel microorganism, which is a new strain of *Xanthomonas campestris*. A deposit under the Budapest Treaty of a biologically pure culture of the microorganism employed in making this heteropolysaccharide was made with the American Type Culture Collection, Rockville, Maryland, on June 19, 1985 under Accession No. ATCC 53159.

The ATCC also performed the taxonomic identification of the bacterial isolate S-657. Internal ATCC data for *Xanthomonas campestris* strains previously characterized by ATCC were consulted as well as various classifications in the published literature including Bergey's Manual of Systematic Bacteriology 1984, Vol. 1, Krug & Holt eds., Williams & Wilkins; D. W. Dye, *N. Zealand J. Med.*, 5, p. 393-416 (1962), and M. P. Starr, *The Genus Xanthomonas in the Prokaryotes*, (1981).

When peritrichous flagella for this Xanthomonas microorganism were confirmed the recent literature was consulted, including Palleroni, N. in Clarke, P. H. and M. H. Richmond (1975), *Genetics and Biochemistry of Pseudomonas* pg. 5-6, Wiley & Sons; Palleroni, N. *Bergey's Manual of Systematic Bacteriology* (1984), pg. 142, Volume 1; Hugh, R. and G. Gilardi in Lennette, Balows, Hausler and Truant, (1980), *Manual of Clinical Microbiology*, pg. 290, American Society for Microbiology; Palleroni, N., M. Doudoroff, R. Y. Stanier, R. E. Solanes and M. Mendel (1970), *Journal of General Microbiology*, Vol. 60: 215-231; Ulitzwr, S. (1975), *Arch. Microbiology*, Vol 104: 285-288; and Shinoda, S. and Okamoto, K. (1977), *Journal of Bacteriology*, Vol. 129: 1266-1271.

After review of the literature, it was determined that the morphological character of polar flagellation for Xanthomonas, which until recently was considered typical, has greatly reduced taxonomic significance because of cases of abnormal (i.e. lateral) flagellation. The organism was therefore classified as *Xanthomonas campestris* because it has the appropriate characteristics.

Typically, *Xanthomonas campestris* produces xanthan gum by pure culture fermentation processes. The carbohydrate portion of xanthan gum contains glucuronic acid and the neutral sugars glucose and mannose. Heteropolysaccharide S-657, which cannot be considered to be a xanthan gum, contains glucose and rhamnose, but not mannose. Thus, a novel strain of *Xanthomonas campestris*, which produces heteropolysaccharide S-657, is provided by ATCC 53159.

A. Characteristics of Colony Morphology

On nutrient agar, colonies appear in two days at 30° C. with a diameter reaching about 0.5-1.0 mm in diameter. The colonies are round, entire, translucent, smooth and light yellow in pigment. With the addition of 1% glucose to nutrient agar, the colonies become mucoid, domed and shining.

B. Characteristics of Cell Morphology

The cell size is about 0.8-1.0×2.0-3.0 μm on nutrient agar, occurring singly in pairs and in long chains. The cells are gram-negative, actively motile rods with tapered ends. Flagella are peritrichous.

C. Physiological and Biochemical Characteristics

Table 3, below, presents the results of numerous biochemical and physiological tests employed in the identification of this microorganism:

TABLE 3

Biochemical and Physiological Test Results for S-657 isolate

| | | | |
|---|---|---|---|
| 4° C. growth | − | Gelatinase | w |
| 25° C. growth | + | Tween 20 hydrolysis | + |
| 30° C. growth | + | Tween 80 hydrolysis | + |
| 37° C. growth | + | Indole | − |
| 41° C. growth | − | Simmons citrate growth | − |
| Fluorescein produced | | Urease | − |
| Pyocyanine produced | − | Nitrate to nitrite | − |
| Yellow non-diff. pigments | + | Nitrate reduction | − |
| Melanin pigment produced | − | Nitrite to nitrogen gas | − |
| pH 6.0 growth | + | Hydrogen sulfide (TSI) | − |
| 1% NaCl growth (+) | + | Lead acetate strip | + |
| 3% NaCl growth (−) | − | Lysine decarboxylase | − |
| 6.5% NaCl growth | − | Arginine (Mollers) | − |
| MacConkey agar growth | − | Ornithine decarboxylase | − |
| Skim milk agar growth | + | Phenylalanine deamination | − |
| Aesculin hydrolysis | + | Lecithinase | − |
| Casein hydrolysis | − | Phosphatase | − |
| Starch hydrolysis | + | Catalase | + |
| Mucoid gr. on glucose agar | + | Oxidase | − |
| 0.1% TTC growth | − | Gluconate oxidation | − |
| 0.02% TTC growth | + | Growth on malonate as SCS | − |
| | | Tyrosine degradation | − |
| | | dl-hydroxybutyrate growth | − |
| | | PHB accumulation | − |
| | | Deoxyribonuclease | w |
| | | Growth on 0.05% cetrimide | − |
| | | Growth on acetate as SCS | + |
| | | Testosterone deg. | − |

| Sole Carbon Sources in Stanier's Mineral Base | | | |
|---|---|---|---|
| L-arabinose | + | L-malate | w |
| cellobiose | + | pelargonate | − |
| D-fructose | w | propionate | − |
| D-glucose | + | quinate | − |
| lactose | + | succinate | w |
| maltose | + | L-+-tartrate | − |
| D-mannitol | − | valerate | − |
| L-rhamnose | − | B-alanine | − |
| D-ribose | − | D-A-alanine | − |
| D-sorbitol | − | betaine | − |
| sucrose | + | glycine | − |
| trehalose | − | L-histidine | − |
| D-xylose | + | DL-norleucine | − |
| adonitol | − | L-proline | − |
| erythritol | − | D-tryptophan | − |
| glycerol | − | L-valine | − |
| ethanol | − | DL-arginine | − |
| geraniol | − | benzylamine | − |
| i-inositol | − | butylamine | − |

TABLE 3-continued

| | | |
|---|---|---|
| sebacic acid | W | putrescine | — |
| acetamide | — | mesconate | — |
| adipate | — | DL-glycerate | — |
| benzoate | — | L-tryptophan | — |
| butyrate | — | | |
| citraconate | — | | |
| D-gluconate | — | | |
| M-hydroxybenzoate | — | | |
| 2-ketogluconate | — | | |
| DL-lactate | — | | |

Carbohydrate Fermentation in O-F Medium

| | | | | |
|---|---|---|---|---|
| Acid from L-arabinose | + | Acid from adonitol | K |
| Acid from cellobiose | + | Acid from dulcitol | K |
| Acid from ethanol | K | Acid from D-galactose | + |
| Acid from D-fructose | + | Acid from inulin | K |
| Acid from D-glucose AO2 | + | Acid from salicin | — |
| Acid from D-glucose AnO2 | — | Acid from D-sorbitol | — |
| Alkaline pH in D-glucose | — | | |
| Acid from glycerol | K | | |
| Acid from i-inositol | K | | |
| Acid from lactose | + | | |
| Acid from maltose | + | | |
| Acid from D-mannitol | K | | |
| Acid from D-mannose | + | | |
| Acid from D-ribose | K | | |
| Acid from sucrose | + | | |
| Acid from trehalose | K | | |
| Acid from D-xylose | + | | |

TTC = triphenyl-tetrazolium chloride
W = weakly positive
+ = acid
K = alkaline
— = no change

EXAMPLE 1

A YM flask seed was started from a 48-hour nutrient agar culture placed on a gyrotary shaker at 30° C. Approximately, 24 hours later this seed was used to inoculate a flask containing $E_1$ medium with 3% hydrolyzed starch as the carbon source. This medium was also placed on a gyrotary shaker at 30° C. Approximately 72 hours later, this flask was noted to have viscous beer, and upon addition of 2 volumes of 99% isopropyl alcohol, a fibrous precipitate was noted.

$E_1$ medium contains 5 g of dipotassium phosphate, 0.1 g of magnesium sulfate, 0.9 g of ammonium nitrate, 0.5 g of Promosoy 100 (an enzymatic digest of soybean meal sold by Central Soya Chemurgy Division), 30 g of dextrose and 1 L of tap water. The pH of the $E_1$ medium is about 7.6–7.8.

Another YM seed flask was prepared in the above fashion and used at 24 hours to inoculate 5 flasks containing various media and these flasks were incubated at 30° C. on a gyrotary shaker for about 72 hours at which time the pH, viscosity, gum yield and product viscosity were measured. The results are shown in Table 4 below.

TABLE 4
Effect of Media on Gum Production

| Medium | Carbon Source | pH | Beer Vis (cP) | % Gum Yield | DI Water Prod Vis (cP) 1%/0.1% | 1% KCL Prod Vis (cP) 1%/0.1% |
|---|---|---|---|---|---|---|
| $E_1$ | 3% hydrolyzed starch | 6.6 | 1700 | 2.12 | ND | ND |
| $E_1$ ($NH_4NO_3$ + 0.19% $NaNO_3$) | 3% hydrolyzed starch | 6.6 | 345 | 1.86 | ND | ND |
| $E_1$ (containing 0.2% Promosoy 100 | 3% hydrolyzed starch | 6.6 | 65 | 2.14 | ND | ND |
| $E_1$ | 3% glucose | 6.6 | 1000 | 1.10 | 560/14 | 560/13 |
| $E_1$ + HoLe Salts[3] | 3% hydrolyzed starch | 6.5 | 1750[2] | 1.20 | 880/33 | 960/32 |

[1] ND: Not determined
[2] Unutilized starch was hydrolyzed with glucoamylase before precipitation with isopropyl alcohol
[3] HoLe salts: An aqueous solution (used at 1 ml/L of medium) comprising

| | Conc. In Final Medium (ppm) | |
|---|---|---|
| $H_3BO_3$ | 0.05 | $B^{+3}$ |
| $MnCl_2.4H_2O$ | 0.5 | $Mn^{-2}$ |
| $FeSO_4$ | 0.5 | $Fe^{+2}$ |
| $CuCl_2$ | 0.01 | $Cu^{-2}$ |
| $ZnCl_2$ | 0.02 | $Zn^{-2}$ |
| $CoCl_2.6H_2O$ | 0.01 | $Co^{-2}$ |
| $Na_2MoO_4.2H_2O$ | 0.01 | $Mo^{-6}$ |
| Sodium Tartrate | 1.8 | |

As seen from the above results, the best growth medium is $E_1$ with 3% hydrolyzed starch and HoLe salts.

EXAMPLE 2

A fermentation procedure for producing large quantities of heteropolysaccharide S-657 is provided.

A 500 ml Erlenmeyer flask containing 100 ml of YM broth (Difco) was inoculated with a loopful of S-657 cells from a 48-hour nutrient agar plate. The flask was incubated for 24 hours at 30° C. on a gyrotary shaker set at 400 rpm. A 1% inoculum was then made into two 500 ml Erlenmeyer flasks containing 100 ml each of seed medium. The seed medium contained:

| | |
|---|---|
| Glucose | 3% |
| $K_2HPO_4$ | 0.5% |
| $NH_4NO_3$ | 0.09% |
| $MgSO_4.7H_2O$ | 0.01% |
| Promosoy 100 | 0.05% |
| HoLe salts | 1 ml/L |

The medium was prepared in tap water. HoLe salts are prepared by adding the following ingredients to one liter of deionized or distilled water:

| | |
|---|---|
| $H_3BO_3$ | 285 mg |
| $MnCl_2.4H_2O$ | 1800 mg |
| $FeSO_4$ | 1360 mg |
| $CuCl_2$ | 26.9 mg |
| $ZnCl_2$ | 20.8 mg |
| $CoCl_2$ | 40.4 mg |
| $Mg_2MoO_4.2H_2O$ | 25.2 mg |
| Sodium tartrate | 1770 mg |

These flasks were incubated at 30° C. on a gyrotary shaker at 400 rpm for 24 hours at which point they were used to inoculate a 5 L fermentor vessel containing 3000 ml (final volume) of the same medium. The fermentation was controlled at 30° C. and the aeration rate at 1 L/minute. The agitation was started at 400 rpm and increased thereafter to ensure good mixing. At 24 hours approximately 2.5 L of this seed were used to inoculate a 70 L fermentor containing 50 L (final volume) of the following medium:

| | |
|---|---|
| Glucose | 3.0% |
| $K_2HPO_4$ | 0.05% |
| $NH_4NO_3$ | 0.09% |
| $MgSO_4.7H_2O$ | 0.01% |
| Promosoy 100 | 0.05% |
| HoLe Salts | 1 ml/L |
| $Fe^{++}$ | 1 ppm |
| Sag 5691 (a defoaming agent supplied by Union Carbide) | 0.005% |

The temperature was maintained at 30° C. and the aeration rate at 10 L/minute until 25 hours into the fermentation where it was adjusted to 20 L/minute. It remained at that rate for the remainder of the fermentation. The pH was controlled at greater than 6.0 by the addition of 40% KOH as needed using an automatic pH control system. The agitation was initially set at 300 rpm and was increased to 550 rpm at 25 hours, to 750 rpm at 48 hours and to 800 rpm at 72 hours. It remained at 800 rpm for the remainder of the fermentation. The results of this fermentation are given in Table 5 below.

TABLE 5

| Age | pH | Beer Viscosity | Gum Yield (g/100 ml) | Residual Carbon Source |
|---|---|---|---|---|
| 0 hours | 7.0 | 5 cP | ND | 3.0% |
| 25 hours | 6.5 | 230 cP | 0.51 | ND |
| 48 hours | 6.2 | 960 cP | 0.80 | 1.27 |
| 72 hours | 6.3 | 2250 cP | 1.22 | 0.70 |
| 116 hours | 6.2 | 3550 cP | 1.64 | 0.24 |
| 141 hours | 7.1 | 4000 cP | 1.63 | 0.17 |

A total of 150 ml of 40% KOH were used to control the pH during the fermentation. The fermentation liquor was heated to approximately 75° C. for 15 minutes and then cooled to approximately 30° C. The fermentation liquor was added to three volumes of 99% isopropanol. The polysaccharide precipitated as a fibrous material which was easily recovered using a sieve. The fibers were dried in a forced air tray drier at 140° F. for 2.5 hours before being milled to a powder.

EXAMPLE 3

Taxonomic identification was accomplished by comparing certain physiological and biochemical characteristics of the isolate S-657 with characteristics typical of *Xanthomonas campestris* identified in Bergey's 1984 Manual and in the results of 28 strains previously characterized by ATCC. The results are shown in Table 6 below.

TABLE 6

| | Bergey's 1984 Manual | ATCC Data* | Isolate S-657 |
|---|---|---|---|
| Esculin | + | + | + |
| $H_2S$ from Peptone | + | | + |
| Urease | − | − | − |
| Growth at 37° C. | + | + | + |
| Acid in O-F Medium: | | | |
| Arabinose | + | + | + |
| Glucose | + | + | + |
| Sucrose | + | + | + |
| Mannose | + | + | + |
| Galactose | + | + | + |
| Cellobiose | + | + | + |
| Fructose | + | + | + |
| Adonitol | − | − | − |
| Mannitol | − | − | − |
| Sorbitol | − | − | − |
| Dulcitol | − | − | − |
| Salicin | − | − | − |
| Inositol | − | − | − |
| Inulin | − | − | − |
| Trehalose | + | 95 | − |
| Utilization as SCS: | | | |
| Acetate | + | 25 | + |
| Citrate | + | + | − |
| Malate | + | + | + |
| Propionate | + | 5 | − |
| Succinate | + | + | + |
| Lactate | + | 40 | − |
| L-tartrate | − | − | − |
| Benzoate | − | − | − |

*Numbers indicated % positive.

EXAMPLE 4

Sea Water Mud Composition

Heteropolysaccharide S-657 is used in muds for oil well drilling. A formula and data for a seawater mud are as follows:

| S-657 | 1 pound | | | | |
|---|---|---|---|---|---|
| Seawater | 1 barrel (42 gal.) | | | | |
| Fann 35 Viscosity Data: | | | | | |
| Speed (RPM) | 3 | 6 | 100 | 200 | 300 | 600 |
| Dial Reading (f1.0 spring) | 7.8 | 8.4 | 12.4 | 14.8 | 17.0 | 22.4 |
| Viscosity (cP) | 780 | 420 | 37.2 | 22.2 | 17.0 | 11.2 |

EXAMPLE 5

Fresh Water Bentonite Mud

Another drilling formulation in which heteropolysaccharide S-657 is functional is as follows:

| S-657 | 1 pound | | | | |
|---|---|---|---|---|---|
| Bentonite | 7 pounds | | | | |
| Fresh Water | 1 barrel | | | | |
| Fann 35 Viscosity Data: | | | | | |
| Speed (RPM) | 3 | 6 | 100 | 200 | 300 | 600 |
| Viscosity (cP) | 1160 | 610 | 48 | 28.2 | 21.6 | 14.5 |

EXAMPLE 6

Solubility in Salt Containing Systems

Heteropolysaccharide is soluble in various salt containing systems. One pound of S-657 is mixed with one barrel (42 gal.) of the following aqueous components and the Fann 35 Viscosity is determined as follows:

| | Fann 35 Viscosity (cP) Data: | | | | | |
|---|---|---|---|---|---|---|
| RPM | 3 | 6 | 100 | 200 | 300 | 600 |
| Fresh Water | 1200 | 540 | 36.0 | 19.8 | 14.6 | 9.2 |
| 3% KCl | 920 | 510 | 42 | 23.7 | 17.6 | 10.4 |
| 15% NaCl | 580 | 320 | 31.2 | 19.2 | 15 | 9.9 |

Other embodiments of the present invention will be apparent to one skilled in the art from a consideration of this specification. It is intended, therefore, that the specification and examples be considered as exemplary only, with the true scope and spirit of the invention being indicated by the following claims.

What is claimed is:

1. Heteropolysaccharide S-657, consisting essentially of carbohydrate, substantially no pyruvate, about 12% protein and about 7% acyl groups calculated as O-acetyl, the carbohydrate portion containing about 19% glucuronic acid, and the neutral sugars rhamnose and glucose in the approximate molar ratio of 2:1 wherein the heteropolysaccharide S-657 is produced by a biologically pure culture of Xanthomonas campestris ATCC 53159 in an aqueous nutrient medium by aerobic fermentation of an assimilable carbon source at a pH greater than 6.0 and a temperature of 25°-35° C.

2. A well treating fluid consisting of water and from about 0.01% to about 1.0% by weight of the heteropolysaccharide S-657 according to claim 1.

* * * * *